United States Patent
Swanda

(10) Patent No.: US 8,772,033 B2
(45) Date of Patent: Jul. 8, 2014

(54) METHODS OF MULTIPLYING PLANT EMBRYOGENIC TISSUE IN A BIOREACTOR

(75) Inventor: Anthony P. Swanda, Federal Way, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 149 days.

(21) Appl. No.: 13/039,638

(22) Filed: Mar. 3, 2011

(65) Prior Publication Data

US 2011/0244444 A1    Oct. 6, 2011

Related U.S. Application Data

(60) Provisional application No. 61/319,763, filed on Mar. 31, 2010.

(51) Int. Cl.
| | | |
|---|---|---|
| *C12N 5/00* | (2006.01) | |
| *A01H 5/00* | (2006.01) | |
| *A01H 7/00* | (2006.01) | |
| *A01H 4/00* | (2006.01) | |
| *C12N 5/04* | (2006.01) | |

(52) U.S. Cl.
CPC ............... *C12N 5/04* (2013.01); *C12N 5/0025* (2013.01); *A01H 4/001* (2013.01); *C12N 2500/34* (2013.01); *A01H 4/005* (2013.01)
USPC .......... 435/430.1; 435/422; 800/298; 800/319

(58) Field of Classification Search
CPC ....... A01H 4/008; A01H 4/005; C12M 41/34; C12M 21/06; C12Q 3/00
USPC .......................... 435/422, 431, 430.1; 800/319
See application file for complete search history.

(56) References Cited

U.S. PATENT DOCUMENTS

| | | | |
|---|---|---|---|
| 5,558,984 A | 9/1996 | Young | |
| 7,435,581 B2 | 10/2008 | West | |
| 7,625,754 B2 * | 12/2009 | Gupta et al. | .................. 435/422 |
| 2005/0019932 A1 | 1/2005 | Dale et al. | |
| 2005/0158701 A1 | 7/2005 | West | |
| 2005/0188436 A1 | 8/2005 | Gupta et al. | |
| 2005/0233448 A1 | 10/2005 | Oh et al. | |
| 2006/0171091 A1 | 8/2006 | Seale et al. | |
| 2009/0253182 A1 | 10/2009 | Huber et al. | |

FOREIGN PATENT DOCUMENTS

| | | |
|---|---|---|
| WO | 2006071716 A2 | 7/2006 |
| WO | 2006086489 A1 | 8/2006 |

OTHER PUBLICATIONS

Dochain. Process control, strategy and optimization. Encyclopedia of Bioprocess Technology: Fermentation, Biocatalysis and Bioseparation 1999, 2048-2056.*
Son et al. Selection and proliferation of rapid growing cell lines from embryo derived cell culture of yew trees (*Taxus cuspidata* Sieb. et Zucc) Biotechnol. Bioprocess Eng. 1999, 4, 112-118.*
Tang et al. Changes in growth parameters of embryogenic cell suspension cultures of Loblolly pine (*Pinus taeda*) Journal of Tropical and Subtropical Botany 1998, 6(1):30-34.*
Tang et al. 1998 English translation, 10 pp.*
Zhang et al. Application of image analysis to fed-batch cultures of somatic embryos. In vitro Cell. Dev. Biol.—Plant 32: 190-198, 1996.*
Folly, R., et al.; Adaptive Control of Feed Load Changes in Alcohol Fermentation, Brazilian Journal of Chemical engineering, Eng. vol. 14 No. 4 San Paulo Dec. 1997, ISSN 0104-6632, Rio de Janerio—Brazil, 11 pp.
Maskow, T., et al.; Observation of non-linear biomass-capacitance correlations: Reasons and implications for bioprocess control, Biosensors and Bioelectronics 24 (2008) 123-128, ISSN: 09565663, Elsevier, Amsterdam.
Shetty, R.; Bioreactor Design and Operation for Clonal Tree Propagation—A Thesis in Chemical Engineering, The Pennsylvania State University The Graduate School The Department of Chemical Engineering, Aug. 2011, Pennsylvnia, US, pp. 1-102.

* cited by examiner

*Primary Examiner* — June Hwu
(74) *Attorney, Agent, or Firm* — Christensen O'Connor Johnson Kindness PLLC

(57) ABSTRACT

The present invention provides methods of multiplying plant embryogenic tissue in a bioreactor.

12 Claims, 4 Drawing Sheets

METHODS OF MULTIPLYING PLANT EMBRYOGENIC TISSUE IN A BIOREACTOR

CROSS-REFERENCE(S) TO RELATED APPLICATION(S)

The present application claims the benefit of U.S. Provisional Application No. 61/319,763, filed Mar. 31, 2010.

FIELD OF THE INVENTION

The present invention relates to methods of multiplying plant embryogenic tissue in a bioreactor.

BACKGROUND

Somatic cloning is the process of creating genetically identical plants from plant tissue other than male and female gametes. In one approach to somatic cloning, plant tissue is cultured in an initiation medium that includes hormones, such as auxins and/or cytokinins, to initiate formation of embryogenic tissue, such as embryonal suspensor masses, that are capable of developing into somatic embryos. The embryogenic tissue is then further cultured in a multiplication medium that promotes establishment and multiplication of the embryogenic tissue to form pre-cotyledonary embryos (i.e., embryos that do not possess cotyledons). The pre-cotyledonary embryos are then cultured in a development medium that promotes development and maturation of cotyledonary somatic embryos which can, for example, be placed on germination medium to produce germinants, and subsequently transferred to soil for further growth, or alternatively, placed within manufactured seeds and sown in soil where they germinate to yield seedlings.

The multiplication (maintenance) stage of somatic cloning of plant tissue in the laboratory is typically carried out in liquid suspension cultures in shake flasks using a batch method, also known as splitting. In the practice of a batch culture method, embryogenic tissue is cultured in liquid multiplication medium for a period of time; the embryogenic tissue is separated from the multiplication medium (e.g., by allowing the embryogenic tissue to settle out of the medium); then aliquots of the embryogenic tissue are removed and introduced into separate volumes of fresh multiplication medium for further culture. This process is repeated as often as desired to yield a multiplicity of containers that each include separate batches of the embryogenic tissue culture. In addition to small volumes and multitudes of containers, it is difficult to control the growth conditions in shake flasks, and there is culture variability between flasks.

Although the batch culture method is useful at laboratory scale, it is impractical to use the batch method for commercial-scale production of somatic embryos. Bioreactors are more suitable for large-scale production and provide several advantages over the shake-flask, batch method, including automation, and the ability to more closely monitor and control the culture environment, such as pH, sugar concentration, dissolved oxygen, and carbon dioxide, resulting in more homogeneous cultures and higher yield of quality somatic embryos than the shake-flask method.

The successful operation of commercial-scale liquid bioreactors for the multiplication of plant embryogenic tissue requires automatic regulation of the biomass concentration. In a production environment, success is achieved by quickly multiplying vigorous embryogenic tissue. A production friendly approach for multiplying plant embryogenic tissue is in a fed-batch bioreactor, where a small volume of plant embryogenic tissue and multiplication media is inoculated into the bioreactor and additional multiplication media is added over time until a sufficient volume of plant embryogenic tissue (biomass) has been achieved or the maximum volume of the bioreactor is reached.

Regulation of the biomass concentration is important as there are strong correlations between biomass concentration and the concentration of media components and extra cellular products in the bioreactor. There are two broad classes of extra-cellular components, those that induce somatic embryogenesis and those that inhibit it. It is well known that a minimum biomass concentration is needed to induce somatic embryogenesis, while it has also been shown that at high biomass concentrations, somatic embryogenesis is inhibited. Key media components that are inversely proportional to biomass concentration are sugar and plant hormones. At high biomass concentrations, both classes of media components can become depleted. The sugar concentration is important as it is the primary osmotic agent in liquid multiplication media.

In order to regulate biomass concentration, multiplication media should be added at a rate that best matches the growth of the biomass. However, this is difficult as the actual growth rate of the biomass may deviate significantly from a priori estimates, and under exponentially increasing biomass growth conditions, the biomass concentration can run away. Another difficulty is that a fed-batch reactor can be inoculated with a small amount of culture and fed media over a long period of time, e.g., multiple weeks, which can lead to significantly under or over feeding the biomass in the bioreactor.

The present invention provides methods of multiplying plant embryogenic tissue in a bioreactor.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present invention provides methods of multiplying plant embryogenic tissue in a bioreactor. The methods of the present invention each includes the steps of (a) inoculating plant embryogenic tissue and multiplication media into a bioreactor; (b) measuring a parameter that is a direct measure of, or correlated to, a concentration of the plant embryogenic tissue in the bioreactor; (c) using the measurement obtained in step (b) to calculate a flow rate of additional multiplication media; (d) delivering additional multiplication media to the bioreactor based on the flow rate calculated in step (c); and (e) periodically repeating steps (b) to (d). Parameters that are a direct measure of, or correlated to, the concentration of plant embryogenic tissue in a bioreactor include dry weight concentration, sugar concentration (measured in Brix), and electrical capacitance. Other parameters may also be measured, such as fresh weight concentration, pH, opacity, conductance, and IR absorption.

The methods of the present invention are useful for multiplying plant embryogenic tissue of any genus/species, including conifer trees such as members of the family Pinacea, including members of the genus *Pinus* (e.g., Loblolly pine (*Pinus taeda*)), or members of the genus *Pseudotsuga* (e.g., Douglas fir (*Pseudotsuga menziesii*)).

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
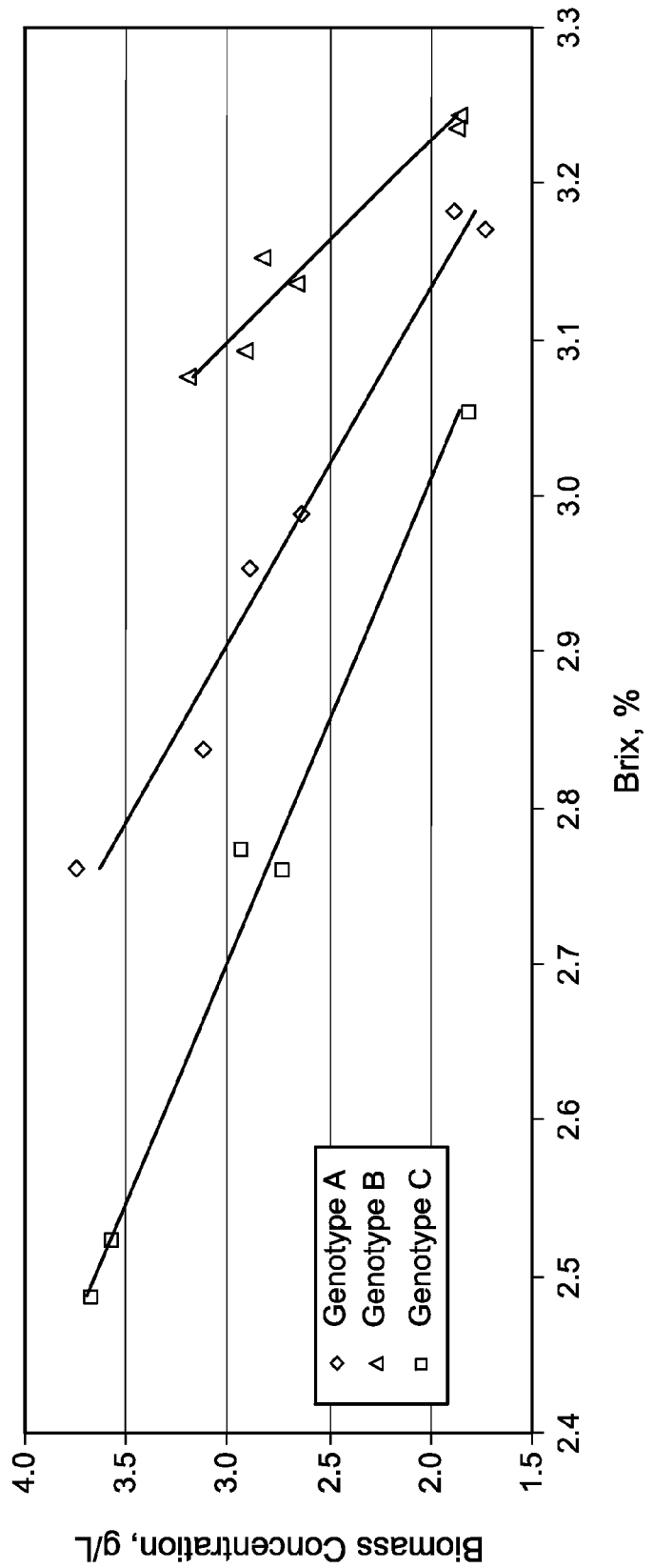
FIG. 1 is a graph illustrating the correlation between the sugar concentration of the culture media in a bioreactor, as measured in percent Brix, and the biomass concentration in the reactor.

As used herein, the term "biomass" refers to plant embryogenic tissue.

As used herein, the term "plant embryogenic tissue" refers to an aggregate of tens to hundreds of cells that form an embryogenic suspensor mass.

As used herein, the term "embryogenic suspensor mass" (ESM) refers to early stage embryos in the process of multiplication by budding and cleavage.

As used herein, the term "fed-batch process" refers to a tissue culture batch process in which a small volume of plant embryogenic tissue and multiplication media is inoculated into a bioreactor and additional multiplication media is added over time until a sufficient volume of biomass has been achieved or the maximum volume of the bioreactor has been reached.

The somatic embryogenesis process is a process to develop plant embryos in vitro, and includes the steps of (1) initiation, to initiate formation of embryogenic tissue, such as embryonal suspensor masses (ESM); (2) multiplication, sometimes referred to as maintenance, to establish and multiply embryogenic tissue to form pre-cotyledonary embryos; (3) development, to develop and form mature cotyledonary somatic embryos; and (4) post development steps such as stratification, germination, placement into manufactured seeds, and transferring to soil for further growth and development.

The present invention is directed to the multiplication stage of the somatic embryogenesis process.

The present invention provides a method of multiplying plant embryogenic tissue in a bioreactor comprising the steps of (a) inoculating plant embryo genic tissue and multiplication media into a bioreactor; (b) measuring a parameter that is a direct measure of, or correlated to, a concentration of the plant embryogenic tissue in the bioreactor; (c) using the measurement obtained in step (b) to calculate a flow rate of additional multiplication media; (d) delivering additional multiplication media to the bioreactor based on the flow rate calculated in step (c); and (e) periodically repeating steps (b) to (d).

In the present invention, plant embryogenic tissue (such as ESM) and multiplication media is inoculated into a bioreactor. The order in which the plant embryogenic tissue and multiplication media is added to the bioreactor is not important. For example, the embryogenic tissue and multiplication media can be added to the bioreactor together in one sample; or alternatively, the tissue can be added to the bioreactor first, followed by the addition of media; or the media can be added to the bioreactor first, followed by addition of the embryogenic tissue.

The multiplication medium is formulated to promote the growth and multiplication of the embryonal suspensor masses. The medium may include hormones. Examples of hormones that can be included in the medium are auxins (e.g., 2,4-dichlorophenoxyacetic acid (2,4-D)) and cytokinins (e.g., 6-benzylaminopurine (BAP)). Auxins can be utilized, for example, at a concentration of from 1 mg/L to 200 mg/L. Cytokinins can be utilized, for example, at a concentration of from 0.1 mg/L to 50 mg/L. The multiplication medium contains nutrients that sustain the embryogenic tissue. It is generally desirable, though not essential, to include maltose as the sole, or principal, metabolizable sugar source in the multiplication medium. Examples of useful maltose concentrations are within the range of from about 2.5% to about 6.0%. The osmolality of the multiplication medium is typically in the range of 100-250 mM/kg. The composition of multiplication media is well-known in the art. Suitable multiplication media can be found, e.g., in Gupta et al., U.S. Pat. No. 7,625,754.

A suitable bioreactor useful in practicing the present invention is the WAVE Biotech 20/50 EH system rocker and WAVE Biotech CELLBAGS. Other rocker systems can also be used, such as ARMA/rock shakers, or Sartorius BIOSTAT bioreactors.

In one embodiment, the plant embryogenic tissue is embryonal suspensor mass. In one embodiment, the plant embryogenic tissue is Loblolly pine. In one embodiment, the plant embryogenic tissue is Douglas fir.

Parameters that are a direct measure of, or correlated to, a concentration of the plant embryogenic tissue biomass concentration a bioreactor include dry weight concentration, sugar concentration (measured in Brix), and electrical capacitance. In one embodiment of the invention, the parameter that is measured is dry weight concentration. In one embodiment, the parameter that is measured is sugar concentration. In one embodiment, the sugar concentration is measured in percent Brix or Brix units. In one embodiment, the parameter that is measured is electrical capacitance. Other parameters may also be measured, such as fresh weight concentration, pH, opacity, conductance, and IR absorption.

Figure 2:
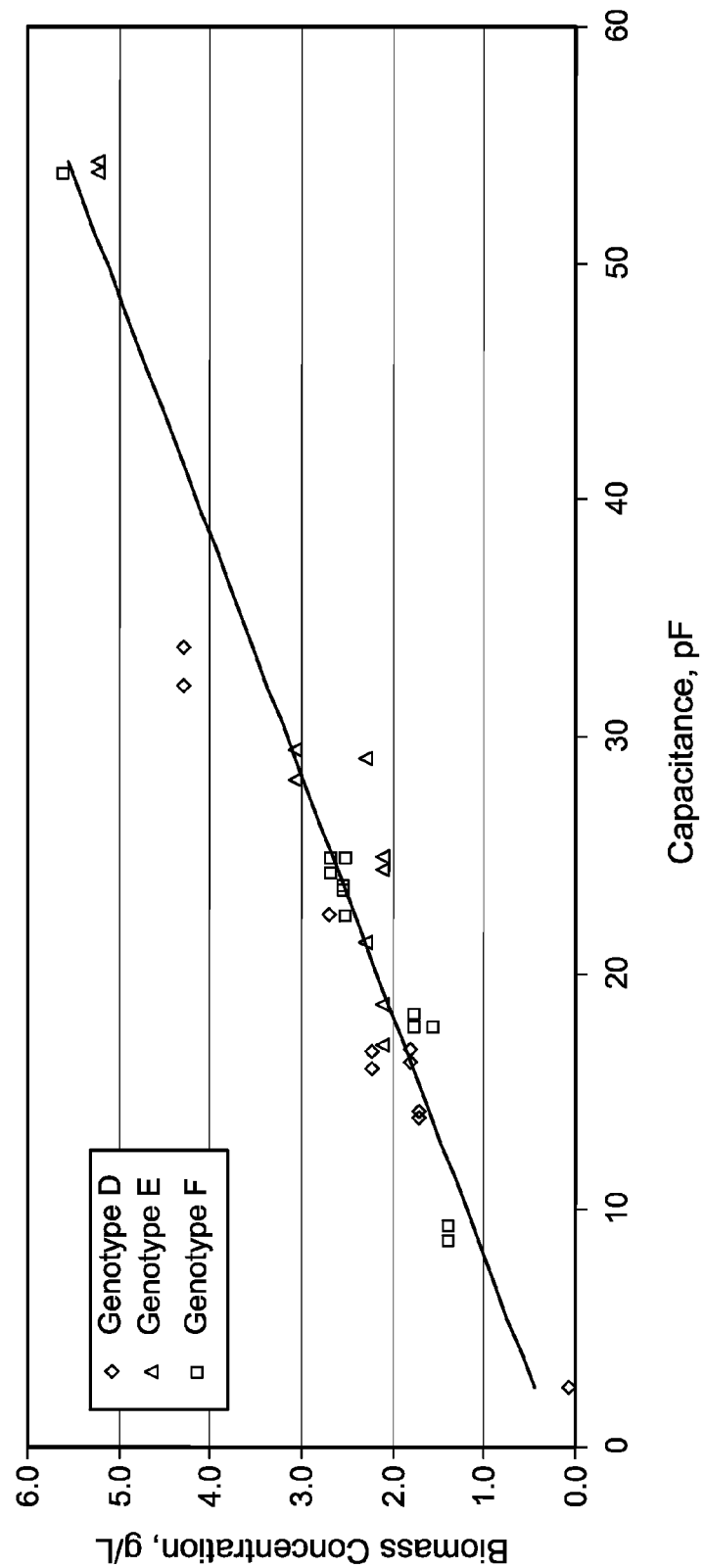
FIG. 2 is a graph illustrating the correlation between the electrical capacitance of the culture media in a bioreactor and the biomass concentration in the reactor.

Dry weight concentration is a parameter that is a direct measure of the concentration of the plant embryogenic tissue in the bioreactor. Sugar concentration and electrical capacitance are proxy variables for the concentration of the plant embryogenic tissue in the bioreactor, in that both measurements correlate with the concentration of the plant embryogenic tissue in the bioreactor, but do not measure the concentration of the plant embryogenic tissue directly. The correlation between Brix and the concentration of the plant embryogenic tissue; and capacitance and the concentration of the plant embryogenic tissue are shown in FIG. 1 and FIG. 2, respectively.

In one embodiment, a model-based approach is used in which recent growth history and inoculum embryogenic tissue biomass are used to calculate a flow rate of additional multiplication media.

In one embodiment, a non-linear, discrete, proportional-integral feedback controller is used to calculate a flow rate of additional multiplication media. A model based feed-back approach is used to tune the controller response and takes into account the nominal growth rate of the embryogenic tissue, thus allowing a systematic approach to tailoring the response of the controller to the particular growth characteristic of different clonal culture lines. The flow rate of additional multiplication media into the bioreactor is exponentially increased to match the growth rate of the embryogenic tissue, thus making the feedback control non-linear in nature.

Additional multiplication media is delivered to the bioreactor based on the calculated flow rate. In one embodiment, the additional multiplication media is delivered to the bioreactor about once per day. In one embodiment, the additional multiplication media is delivered to the bioreactor about hourly. In one embodiment, the multiplication media is continuously delivered to the bioreactor.

The composition of the additional multiplication media added to the bioreactor may be the same as the composition of the multiplication media used in the initial inoculation of the bioreactor. The composition of the additional multiplication media added to the bioreactor may be different than the composition of the multiplication media used in the initial inoculation of the bioreactor. The composition of the additional multiplication media added to the bioreactor may remain the same throughout the process, or may vary.

Dry Weight Concentration.

In one embodiment of the present invention, the measured parameter is dry weight concentration. Measurement of dry weight concentration provides a method of directly determining the concentration of the plant embryogenic tissue in the bioreactor. Dry weight concentration may be determined by removing a culture sample from the bioreactor; removing the media from the tissue using vacuum filtration; rinsing the tissue; and drying the tissue in an oven, e.g., at 60° C. for 24 hours; and then weighing the dried sample.

When the measured parameter is dry weight concentration, the flow rate of additional multiplication media may be determined using the following equation:

$$f = -\frac{100}{\Delta B_{target}} \frac{x_o k_{eff}}{Y_{x/s}} \exp(k_{eff} t) \quad (1)$$

where $\Delta B_{target}$ is the difference between the target culture supernatant Brix and the Brix of the fresh media to be added, i.e., $B_{sp} - B_m$. $Y_{x/s}$ is the amount of biomass produced divided by the amount of sugar consumed. Time (t)=0 at the start of a fed-batch, and t=$t_f$ at the end of the fed-batch. The flow rate of additional multiplication media can be specified to achieve a target $\Delta B$ that will result in a target culture biomass concentration.

To determine $x_o$ and $k_{eff}$, culture volume and biomass concentration is measured at the start and end of each batch. Biomass is determined using the following equation:

$$x = V \cdot X \quad (2)$$

where V is culture volume and X is dry weight biomass concentration.

An estimate of the effective growth rate is determined using the following equation:

$$k_{eff} = \frac{1}{t_f} \ln\left(\frac{V_f X_f}{V_o X_o}\right) \quad (3)$$

where $V_o$ and $V_f$ are initial and final culture volume, respectively; and $X_o$ and $X_f$ are initial and final dry weight biomass concentration, respectively; and $t_f$ is the time in days between the start and end of a batch. This method is repeated for each serial fed-batch.

Sugar Concentration.

In one embodiment of the present invention, the measured parameter correlated to a concentration of the plant embryogenic tissue in the bioreactor is sugar concentration. The sugar concentration may be measured as a percent in units of Brix, which is grams sugar per 100 grams solute. The Brix measurement is inversely proportional to the biomass concentration. A low Brix reading reflects a low sugar concentration and indicates a high biomass; conversely, a high Brix reading reflects a high sugar concentration and indicates a low biomass. It is desirable to control the sugar concentration in the media in the bioreactor to maintain the biomass concentration within a narrow range, thus optimizing the conditions in the bioreactor to ultimately increase the yield and quality of the biomass.

The sugar concentration in the media in the bioreactor is controlled by using a fed-batch process. Initially, plant embryogenic tissue and multiplication media are inoculated into the bioreactor. As the embryogenic tissue multiplies, multiplication media must be added to the reactor or the biomass will concentrate. In the fed-batch phase of operation of the bioreactor, the amount of multiplication media added to the bioreactor is controlled, thereby controlling biomass concentration. In one embodiment of the present invention, the flow rate of additional multiplication media into the bioreactor is controlled by using a non-linear discrete, proportional integral feedback controller.

The sugar concentration of the culture media is periodically measured. The sugar concentration can be measured, for example, daily, semi-weekly, or weekly. One method of measuring the sugar concentration is to draw a supernatant sample from the bioreactor and use a bench-top refractometer to measure Brix. Another method of measuring the sugar concentration is to place an in-situ refractometer probe into the bioreactor. An optimal Brix value or set point is predetermined. If Brix is trending above the set point, the amount of multiplication media added to the culture is reduced. If Brix is trending below the set point, the amount of multiplication media added is increased. The amount of media added is controlled by controlling the flow rate of media to the bioreactor.

When the measured parameter is Brix, the flow rate of additional media may be determined using the following equation:

$$f = V_o \cdot k_f \exp(k_f t) \quad (4)$$

where f is the flow rate in milliliters per day; $V_o$ is the volume of the bioreactor in milliliters at t=0; $k_f$ is the flow rate factor (per day); t is the current time; and t has units of days.

The flow rate factor, $k_f$ is determined using the following equation:

$$k_f^n = k_f^{n-1} + K_c\left[(B^{n-1} - B^n) + \frac{\Delta t}{\tau_I}(B_{sp} - B^n)\right] \quad (5)$$

where n is the current sample time, n−1 is the previous sample time, $k_f$ is the flow rate factor (per day); $K_c$ is the controller gain, per percent day; B is the Brix value of the current sample; $B_{sp}$ is the target Brix value; $\Delta t$ is the time between Brix samples (in days); and $\tau_I$ is the controller reset, day.

The Brix value of the current sample and the Brix set point or target value are inputs to the controller while the flow rate factor is the controller output.

Several other calculations are included with the controller, to guide the operator/engineer in tuning the feedback controller. The following controller tuning is recommended and it is a model-based approach:

$$K_c = \frac{1}{(B_m - B_{sp})\lambda} \quad (6)$$

$$\tau_I = \frac{1}{k_{eff}} \quad (7)$$

where $\lambda$ is the desired closed loop time constant and $k_{eff}$ is the nominal effective growth rate. Lambda is recommended to be $1/k_{eff} \leq \lambda \leq 3/k_{eff}$.

Equation (5) above is one example of the linear portion of a discrete proportional-integral controller that is useful in the practice of the claimed invention. Other forms of proportional-integral-derivative controllers may also be used.

Equation (4) above is one example of the non-linear portion of a discrete proportional-integral controller that is useful in the practice of the claimed invention. The non-linear portion of the controller is based on a first order growth kinetic; i.e., the flow rate is exponentially increasing over time. However, other growth kinetics could be assumed, which would modify the equation for the flow rate.

Equation (4) calculates the flow rate of additional multiplication media in milliliters per day. In practice, the calculated amount of media to be added per day can be dosed in a single dose once a day, or fractional amounts can be added periodically, for example, every hour, or alternatively, the media can be continuously added into the bioreactor.

Advantages of measuring and controlling culture Brix include: only a small sample of culture supernatant (as little as a milliliter) is required, and Brix measurements can be taken quickly. An additional benefit of regulating Brix is that the sugar concentration, and thus the osmotic potential of the media in the bioreactor, is being directly controlled.

Capacitance.

In one embodiment of the present invention, the measured parameter correlated to a concentration of the plant embryogenic tissue in the bioreactor is the electrical capacitance of the culture at low radio frequencies. Capacitance relates directly to the concentration of living biomass with healthy cell membranes. The electrical capacitance of suspension cultures are typically measured using an alternating current at low radio frequencies between 100 kHz and 20 Mhz using commercially available instruments. Similar to the method for the Brix feedback controller, flow rate of additional media may be calculated using Equation (4), where the flow rate factor $k_f$ is determined using the following equation:

$$k_f^n = k_f^{n-1} - K_c\left[(C^{n-1} - C^n) + \frac{\Delta t}{\tau_I}(C_{sp} - C^n)\right] \quad (8)$$

where n is the current sample time, n−1 is the previous sample time; $k_f$ is the flow rate factor (per day); $K_c$ is the controller gain, per pF day; C is the capacitance value of the current sample and it has units of picofarads; $C_{sp}$ is the target capacitance value; $\Delta t$ is the time between capacitance samples (in days); and $\tau_I$ is the controller reset, day.

Equation (4) calculates the flow rate of additional multiplication media in milliliters per day. In practice, the calculated amount of media to be added per day can be dosed in a single dose once a day, or fractional amounts can be added periodically, for example, every hour, or alternatively, the media can be continuously added into the bioreactor.

EXAMPLES

The following examples are provided to illustrate, not limit, the invention.

Example 1

This Example provides an example of calculations that may be used to determine the media flow rate when the measured parameter is dry weight concentration.

$$f = -\frac{100}{\Delta B_{target}} \frac{x_o k_{eff}}{Y_{x/s}} \exp(k_{eff} t) \quad (1)$$

$$x = V \cdot X \quad (2)$$

$$k_{eff} = \frac{1}{t_f} \ln\left(\frac{V_f X_f}{V_o X_o}\right) \quad (3)$$

1. Determine $Y_{x/s}$ experimental or consult literature for anticipated $Y_{x/s}$.
2. Select $\Delta B_{target}$.
3. Determine $k_{eff}$ using Equation (3) and $V_o$, $V_f$, $X_o$, $X_f$, and $t_f$ from the previous fed-batch (a sample of which is being used to inoculate the current fed-batch).
4. Set $X_o$ (for the current fed-batch)=$X_f$ (from the previous fed-batch).
5. Inoculate with $V_i$ and set $V_o$ (for the current batch)=$V_i$.
6. Determine $x_o$ using Equation (2) and $X_o$ and $V_o$ from Steps 4 and 5, respectively.
7. Set t=0 and start timer, t.
8. Determine and implement f continuously or periodically using Equation (1) until the end of the fed-batch, i.e., until t=$t_f$.
9. Measure $V_f$ and $X_f$.
10. Repeat Steps 3-9 for each subsequent fed-batch.

Example 2

This Example provides an example of calculations that may be used to determine the media flow rate when the measured parameter is sugar concentration (Brix).

$$f = V_o \cdot k_f \exp[k_f t] \quad (4)$$

$$k_f^n = k_f^{n-1} + K_c\left[(B^{n-1} - B^n) + \frac{\Delta t}{\tau_I}(B_{sp} - B^n)\right] \quad (5)$$

$$K_c = \frac{1}{(B_m - B_{sp})\lambda} \quad (6)$$

$$\tau_I = \frac{1}{k_{eff}} \quad (7)$$

1. Determine $k_{eff}$ experimental or consult literature for anticipated $k_{eff}$.
2. Select $B_{sp}$.
3. Select or determine $K_c$ and $\tau_I$:
   a. If using Equations 6 and 7 to determine $K_c$ and $\tau_I$,
      i. use $k_{eff}$ and $B_{sp}$ from Steps 1 and 2, respectively,
      ii. measure $B_m$,
      iii. select $\lambda$.
4. Select $\Delta t$.
5. For n=1 (first Brix sample):
   a. Set $k_f^0 = k_{eff}$,
   b. Measure B, c. Set $B^1=B$,
d. Set $B^0=B$,
e. Determine $k_f^1$ using Equation 5,
f. Set $V_o=V$,
g. Set $t=0$ and start timer, t,
h. Determine and implement f continuously or periodically using Equation (4), and $V_o$ from Step 5f, and $k_f=k_f^1$ from Step 5e, until the next Brix measurement is taken.
6. For $n \geq 2$ (all subsequent Brix measurements):
a. Measure B,
b. Set $B^n=B$,
c. Determine $k_f^n$ using Equation 5,
d. Set $V_o=V$,
e. Set $t=0$ and start timer, t,
f. Determine and implement f continuously or periodically using Equation (4), and $V_o$ from Step 6d, and $k_f=k_f^n$ from Step 6c, until the next Brix measurement is taken.
7. Repeat Step 6.

Example 3

This Example provides an example of calculations that may be used to determine the media flow rate when the measured parameter is capacitance.

$$k_f^n = k_f^{n-1} - K_c \left[ (C^{n-1} - C^n) + \frac{\Delta t}{\tau_I}(C_{sp} - C^n) \right] \quad (8)$$

1. Determine $k_{eff}$ experimental or consult literature for anticipated $k_{eff}$.
2. Select $B_{sp}$, $K_c$, $\tau_I$, and $\Delta t$.
3. For $n=1$ (first capacitance measurement):
a. Set $k_f^0=k_{eff}$,
b. Measure C,
c. Set $C^1=C$,
d. Set $C^0=C$,
e. Determine $k_f^1$ using Equation (8),
f. Set $V_o=V$,
g. Set $t=0$ and start timer, t,
h. Determine and implement f continuously or periodically using Equation (4), as in Example 2, and $V_o$ from Step 3f, and $k_f=k_f^1$ from Step 3e, until the next capacitance measurement is taken.
4. For $n \geq 2$ (all subsequent capacitance measurements):
a. Measure C,
b. Set $C^n=C$,
c. Determine $k_f^n$ using Equation 9,
d. Set $V_o=V$,
e. Set $t=0$ and start timer, t,
f. Determine and implement f continuously or periodically using Equation (4), and $V_o$ from Step 4d, and $k_f=k_f^n$ from Step 4c, until the next capacitance measurement is taken.
5. Repeat Step 4.

Example 4

This Example shows the control of sugar concentration in the culture media in a bioreactor when the flow rate of additional media is not calculated using a proportional integral controller.

In this Example, a WAVE Biotech 20/50 EH system rocker and WAVE CELLBAG, available from GE Healthcare, were used. Embryonal suspensor mass of two genotypes of Loblolly pine, genotype A, and genotype B, were each multiplied in a 2 liter CELLBAG.

For genotype A, a 2 L CELLBAG was inoculated with 20 ml of settled cell volume (SCV) and 80 ml of fresh media. For genotype B, a 2 L CELLBAG was inoculated with 40 ml of SCV and 160 ml of fresh media. Both genotypes were cultured using the same multiplication medium, and were cultured for a period of 3 weeks. In one treatment T2, the CELLBAGS were maintained at 20° C.; in another treatment T3, the CELLBAGS were maintained at 25° C.

No culture media was added to the bioreactors for Days 0-5. On Days 5-7, the rate of addition of media to the bioreactors was 1.2 mL per hour; Days 7-14, the rate was 1.9 mL per hour; and Days 14-21, the rate was 4.2 mL per hour. Media addition rates were based on an estimate of the amount of biomass present in the bioreactor, and the total amount of media to be added over a week's time was 4 times the estimated amount of biomass present in the bioreactor.

Figure 3:
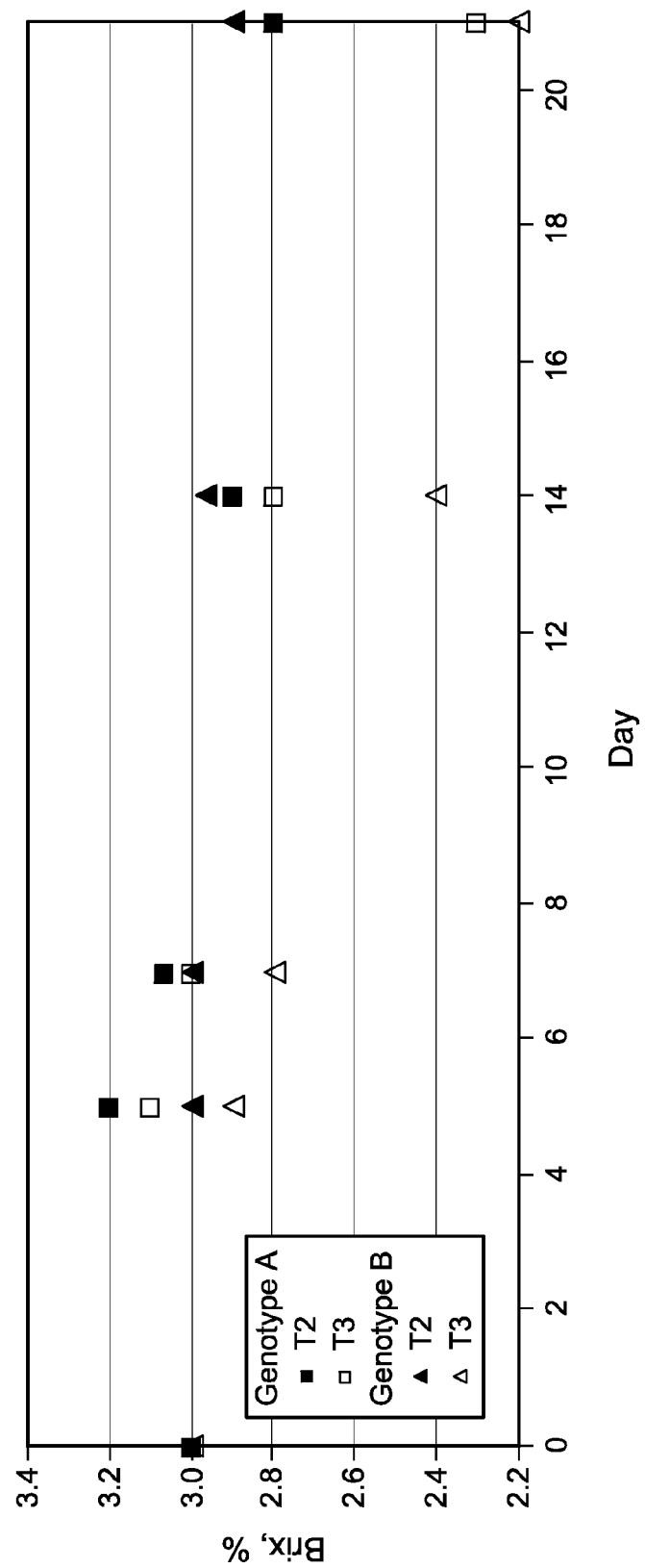
FIG. 3 is a graph illustrating the sugar concentration of the culture media in a bioreactor, as measured in Brix, over a period of time, where the amount of multiplication media added to the culture is estimated and not calculated by a proportional-integral controller.

Samples of supernatant were removed from the bioreactor on Day 0, 2, 5, 7, 14, and 21, and Brix was measured. The sugar concentration of the culture medium, as measured in Brix, over the culture period is shown in FIG. 3. As can be seen in FIG. 3, starting around Day 5, which is when media addition started, Brix measurement for both genotypes trended down. The results show that sugar concentration was not well controlled in this experiment in which the amount of media added was a multiple of the estimated amount of biomass in the reactor.

Example 5

This Example shows the control of sugar concentration in the culture media in a bioreactor when the flow rate of additional media is calculated using a proportional integral controller.

In this example a discrete PI (proportional-integral) feedback controller was used to control the Brix of culture supernatant. Brix was measured frequently during the culture cycle and the rate of media addition was adjusted after each measurement using Equations (4) and (5) to drive Brix to a target value. Target Brix values were determined based on target culture biomass concentrations.

In this Example, the embryonal suspensor mass of genotype C of Loblolly pine was multiplied in a 2 liter WAVE CELLBAG, and a WAVE Biotech 20/50 EH system rocker was used.

The CELLBAGS were inoculated with 300 ml of genotype C culture. The target Brix values were as follows: Treatment 1—2.77%; Treatment 2—2.50%; and Treatment 3—3.03%. Each Treatment was run in duplicate. The sugar concentration of the culture medium, as measured in Brix, over the culture period is shown in FIG. 4.

Figure 4:
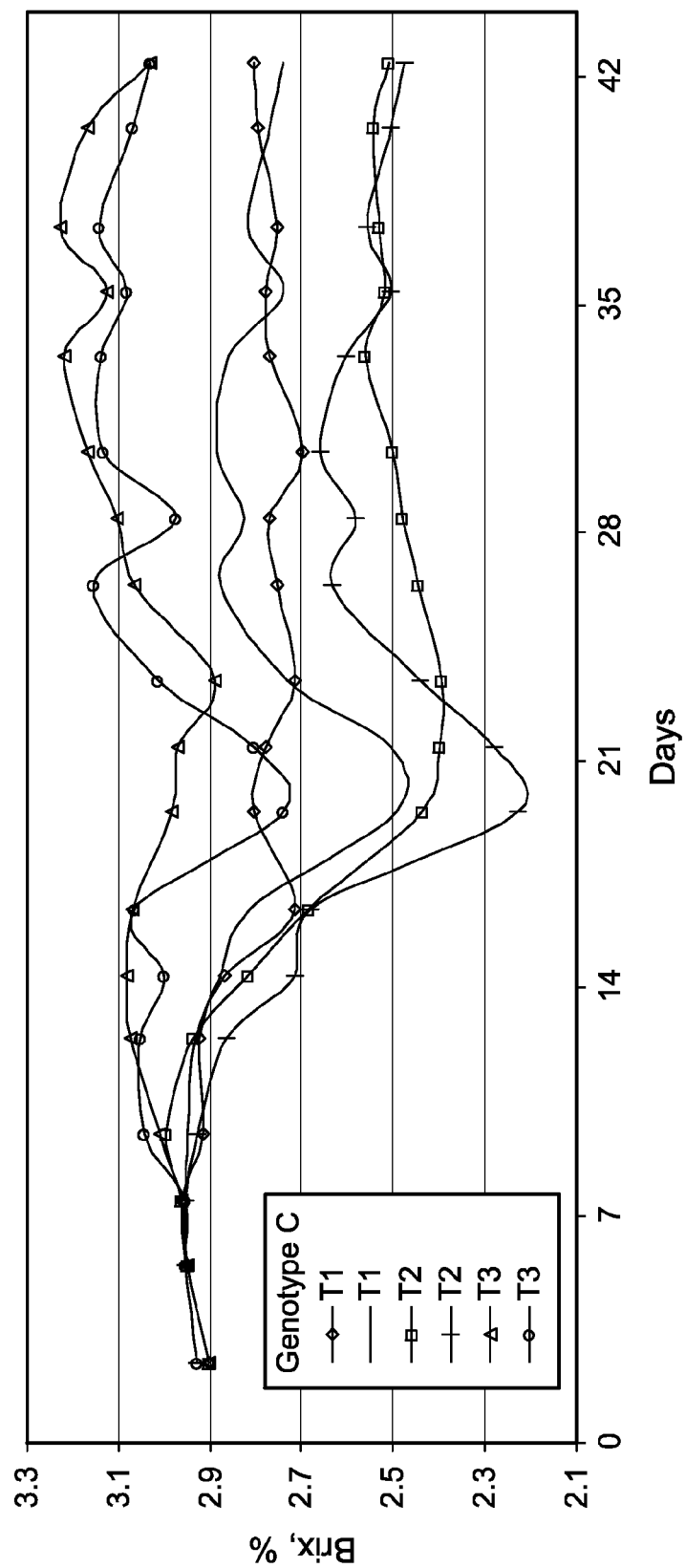
FIG. 4 is a graph illustrating the sugar concentration of the culture media in a bioreactor, as measured in Brix, over a period of time, when the amount of multiplication media added to the culture is calculated by a proportional-integral controller.

As can be seen in FIG. 4, the PI controller was fairly successful in achieving and maintaining the target Brix values. The sharp decrease in Brix values around Day 21 was due to a media system malfunction, where no media was added to one block of treatments. The other block of treatments was unaffected and they received media as programmed. The affected treatments recovered and by Days 35 and 42 both duplicate samples were close to the target Brix value. In a production environment, process upsets are somewhat common due to equipment failures, operator error, and changing media feed stocks. As this example demonstrates, a bioreactor can quickly return to target operating conditions following a process upset.

While the present invention has been illustrated and described, it will be appreciated that various changes can be made therein without departing from the spirit and scope of the invention.

The invention claimed is:

1. A method of multiplying plant embryogenic tissue in a bioreactor comprising the steps of:
   (a) inoculating plant embryogenic tissue and multiplication medium into a bioreactor;
   (b) measuring a parameter that is a direct measure of, or correlated to, a concentration of the plant embryogenic tissue in the bioreactor;
   (c) determining a target value of the parameter;
   (d) taking the measurement obtained in step (b) and the target value determined in step (c) to calculate a flow rate of additional multiplication medium,
   wherein when the parameter is dry weight concentration, the flow rate of additional multiplication medium is calculated using the equation:

$$f = -\frac{100}{\Delta B_{target}} \frac{x_o k_{eff}}{Y_{x/s}} \exp(k_{eff} t)$$

wherein $\Delta B_{target}$ is the difference between a Brix value of a target culture supernatant ($B_{sp}$) and a Brix value of fresh medium to be added ($B_m$); $Y_{x/s}$ is an amount of biomass produced divided by an amount of sugar consumed; biomass (x) is culture volume (V) multiplied by dry weight biomass concentration (X); $x_0$ is the initial biomass; $k_{eff}$ is effective growth rate; and t is time;
   wherein when the parameter is sugar concentration, Brix or electrical capacitance, the flow rate of additional multiplication medium is calculated using the equation:

$$f = V_o \cdot k_f \exp[k_f t]$$

wherein $V_o$ is an initial volume of a bioreactor, $k_f$ is a flow rate factor, and t is time;
   wherein a proportional integral feedback controller is used to calculate the flow rate factor, and wherein the proportional integral feedback controller is a non-linear, discrete proportional integral controller;
   (e) delivering additional multiplication medium to the bioreactor based on the flow rate calculated in step (d); and
   (f) periodically repeating steps (b) to (e).

2. The method of claim 1, wherein the parameter is dry weight concentration.

3. The method of claim 1, wherein the parameter is selected from the group comprising sugar concentration, Brix, and electrical capacitance.

4. The method of claim 1, further comprising tuning the feedback controller.

5. The method of claim 1, wherein the plant embryogenic tissue is embryonal suspensor mass.

6. The method of claim 1, wherein the additional multiplication medium is delivered to the bioreactor about once per day.

7. The method of claim 1, wherein the additional multiplication medium is delivered to the bioreactor about hourly.

8. The method of claim 1, wherein the additional multiplication medium is continuously delivered to the bioreactor.

9. The method of claim 1, wherein the plant embryogenic tissue is Loblolly pine.

10. The method of claim 2, wherein the effective growth rate ($k_{eff}$) is calculated using the equation:

$$k_{eff} = \frac{1}{t_f} \ln\left(\frac{V_f X_f}{V_o X_o}\right)$$

wherein $V_0$ and $V_f$ are initial and final culture volume, respectively; $X_0$ and $X_f$ are initial and final dry weight biomass concentration, respectively; and $t_f$ is time in days between start and end of a batch.

11. The method of claim 3, wherein the parameter is Brix, and wherein the flow rate factor ($k_f$) is determined using the following equation:

$$k_f^n = k_f^{n-1} + K_c\left[(B^{n-1} - B^n) + \frac{\Delta t}{\tau_I}(B_{sp} - B^n)\right]$$

wherein n is a current sample time; n−1 is a previous sample time; $K_c$ is controller gain; B is a Brix value of a culture supernatant sample; $B_{sp}$ is a target Brix value; $\Delta t$ is a time between Brix samples; and $\tau_I$ is a controller reset day.

12. The method of claim 3, wherein the parameter is electrical capacitance, and where the flow rate factor ($k_f$) is determined using the equation:

$$k_f^n = k_f^{n-1} + K_c\left[(C^{n-1} - C^n) + \frac{\Delta t}{\tau_I}(C_{sp} - C^n)\right]$$

wherein n is a current sample time; n−1 is a previous sample time; $K_c$ is a controller gain; C is a capacitance value of a culture supernatant sample; $C_{sp}$ is a target capacitance value; $\Delta t$ is a time between capacitance sample; and $\tau_I$ is a controller reset day.

* * * * *